(12) United States Patent
Rypaas et al.

(10) Patent No.: US 6,488,699 B1
(45) Date of Patent: Dec. 3, 2002

(54) COOLING DEVICE

(76) Inventors: Gro-Johanne Rypaas, Sven Svensensvei 8, Drammen N-3014 (NO); Stein Rypaas, Sven Svensensvei 8, Drammen N-3014 (NO)

(*) Notice: Subject to any disclaimer, the term of this patent is extended or adjusted under 35 U.S.C. 154(b) by 0 days.

(21) Appl. No.: 09/581,251

(22) PCT Filed: Jan. 14, 1999

(86) PCT No.: PCT/NO99/00012
§ 371 (c)(1),
(2), (4) Date: Jun. 26, 2000

(87) PCT Pub. No.: WO99/36012
PCT Pub. Date: Jul. 22, 1999

(30) Foreign Application Priority Data

Jan. 16, 1998 (NO) .......................... 19980205

(51) Int. Cl.[7] ................ A61F 7/12; A61F 7/00
(52) U.S. Cl. ............... 607/113; 607/96; 607/114
(58) Field of Search ............ 607/96, 113, 114; 606/234–236, 20, 21; 604/285

(56) References Cited

U.S. PATENT DOCUMENTS

| | | | | |
|---|---|---|---|---|
| 2,514,844 A | * | 7/1950 | Cohen | 446/267 |
| 3,885,403 A | | 5/1975 | Spencer | 62/530 |
| 4,563,182 A | * | 1/1986 | Stoy et al. | 424/436 |
| 4,983,122 A | | 1/1991 | Mitnick | 433/229 |
| 5,267,862 A | | 12/1993 | Parker | 433/215 |
| 5,320,114 A | | 6/1994 | Kittelsen et al. | 128/861 |
| 5,460,527 A | | 10/1995 | Kittelsen | 433/215 |
| 5,494,441 A | | 2/1996 | Nicholson | 433/215 |
| 5,682,904 A | | 11/1997 | Stinnett | 128/861 |
| 5,782,868 A | * | 7/1998 | Moore et al. | 606/235 |

* cited by examiner

*Primary Examiner*—Roy D. Gibson
(74) *Attorney, Agent, or Firm*—Jacobson Holman PLLC

(57) ABSTRACT

A cooling product, with a body with a size and shape conforming with the palate, preferably on two plate sides. The body is made of soft material and is filled with an agent which can store cold preferably in gel form, and is mounted on a holder in the form of a shank which prevents the body from being swallowed.

3 Claims, 2 Drawing Sheets

FIG. 2A
FIG. 2B
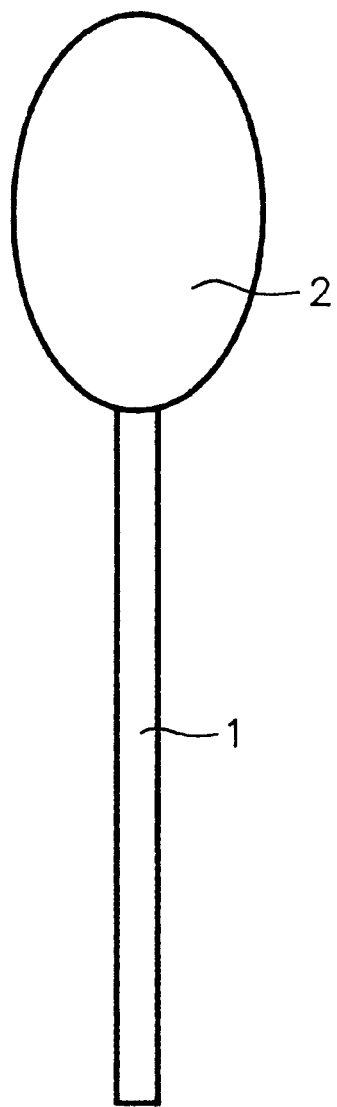
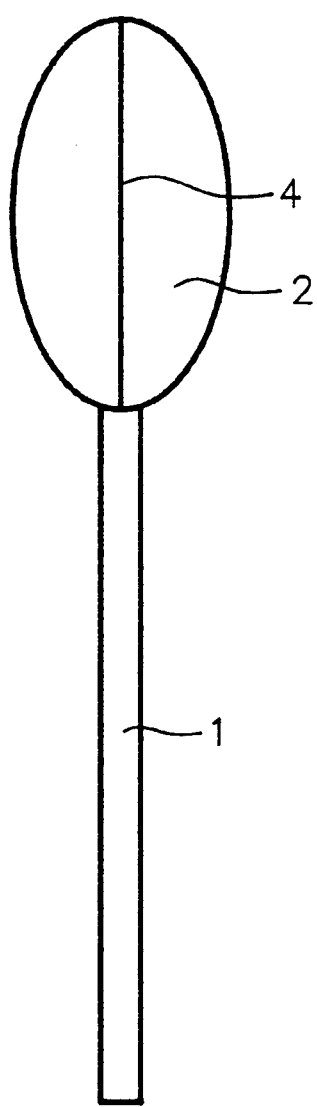

COOLING DEVICE

FIELD OF THE INVENTION

The present invention concerns a cooling device for use in the treatment of problems in swallowing caused, amongst other things, by cerebral palsy or stroke, wherein the device consists of a body made of soft material and filled with an agent which can store cold, preferably in gel form.

BACKGROUND OF THE INVENTION

Patients suffering from, e.g., cerebral palsy usually have problems with swallowing, since their swallowing musculature is not as mobile as that of healthy people. The same problem occurs in stroke patients.

Cooling of the palate area has been shown to be an effective solution to problems in swallowing in these cases. Cooling is normally effected by using a metal spoon which is cooled down before being placed against the palate.

The use of a metal spoon has several drawbacks. First of all, the spoon is hard and does not conform to the shape of the palate, leading to inadequate cooling. In addition to this the spoon is warmed up quickly during use, since the metal has little "thermal inertia". In order to obtain a satisfactory result when using the spoon, one must have at one's disposal several spoons, which are replaced as they become heated to body temperature. This represents much too great a demand on the nursing personnel, who are generally already overtaxed.

Another possible solution to the problem is to use an ice cube placed round a stick. In this case the problem is that the ice cube can fall off the stick, causing the patient to choke.

There are known devices for cooling body parts.

U.S. Pat. No. 4,389,122 discloses a device for use as a hot or cold compress. It comprises a mouthpiece provided with bags filled with a heat/cold storage medium. Even though the device fulfills the function of cooling specific parts of the oral cavity, it is not suitable for palate cooling. The reason is that it has to be adapted to a specific size of palate, i.e. several sizes must be available in store, it is uncomfortable to have in the mouth for long periods, and it is relatively complicated to manufacture and will therefore have a high sales prices. In addition, it is difficult to use in patients who have dental plates, tubes etc. in their mouths, since it may come into contact with the actual plate or its fixing means, causing displacement and discomfort.

U.S. Pat. No. 3,885,403 discloses a device of use as a cold or hot compress. The device comprises a plastic envelope with a gel which maintains a gel-like consistency over large temperature ranges. This compress is not suitable for use in cooling of the palate, since it has to be relatively large in order to avoid the risk of being swallowed, making it uncomfortable in use.

U.S. Pat. No. 5,267,862 discloses a device for treatment of sleep apnea. In connection with the manufacture of the device a dental tray with a handle is employed. The area of application of this device differs from the area of application of the invention. Moreover, the device cannot be moved in the mouth in order to cool different areas in it.

U.S. Pat. No. 5,320,114 discloses a device for fitting mouthguards. The device has a handle and a curved surface for fitting the mouthguard. The area of application of this device is not the same as for the invention.

U.S. Pat. No. 5,460,527 discloses another dental tray which will be employed for bleaching the teeth. The dental tray has a handle which is used for dipping the tray into boiling water and which is later removed. In the same way as for the device described in U.S. Pat. No. 4,983,222 this patent further concerns an object which is intended to be stationary in the mouth, and not a body which is to be moved freely.

As mentioned above, the said known solutions have several disadvantages, and are not satisfactory for use either on the part of the patient or the nurse.

SUMMARY OF THE INVENTION

The above-mentioned problems are solved in a novel and surprising manner with a cooling device in accordance with the invention. The device according to the invention comprises a body made of soft material and filled with an agent which can store cold, preferably in gel form. The device is characterized in that the body is designed in such a way that it can be moved in the oral cavity and in the lip area in order to cool one area at a time, that the body is symmetrical in relation to a median plane, and that it is mounted on a holder in the form of a shank which prevents the body from being swallowed.

By means of the invention parts of the mouth can be cooled in a simple and satisfactory manner.

In one possible embodiment of the invention the cooling body can be divided in two by a central plate, and the plate can be heat-insulating, with the result that when one side of the device has become warm, it can be turned and the other side can be used.

The addition of a holder leads to a substantial reduction in the risk of swallowing the device. This in turn permits the cooling body to be made in a relatively small size. The advantages of a small cooling body are, amongst other things, that it is more comfortable to have in the mouth and that it will not necessarily come into contact with dental plates, or any probes in the mouth, etc. Another advantage of a small cooling body is that it is not necessary to adapt it to different palate sizes and shapes, since the cooling body will. only be in contact with part of the palate, and not the entire palate. Thus it is sufficient to manufacture the device in two sizes, one for children and one for adults.

The holder for the body may be attached to a ring round the cooling body, the ring providing the body with a certain rigidity which makes the device simpler to use. It may also be attached to said central plate.

BRIEF DESCRIPTION OF THE DRAWINGS

The device will now be described in more detailed by means of the attached drawing in which FIGS. 2A and 2B illustrate a front and a side view of a second embodiment of the invention.

DETAILED DESCRIPTION OF THE PREFERRED EMBODIMENTS

Figure 1A:
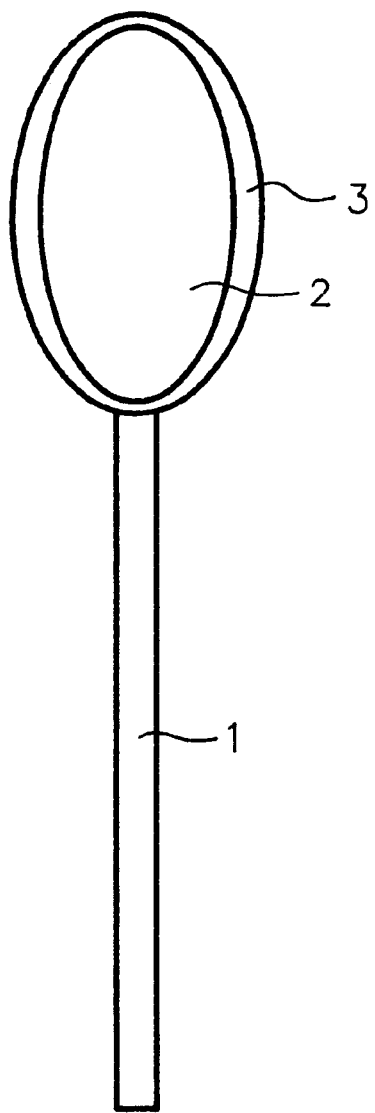
FIGS. 1A and 1B illustrate a front and a side view of a first embodiment of the invention.
Figure 1B:
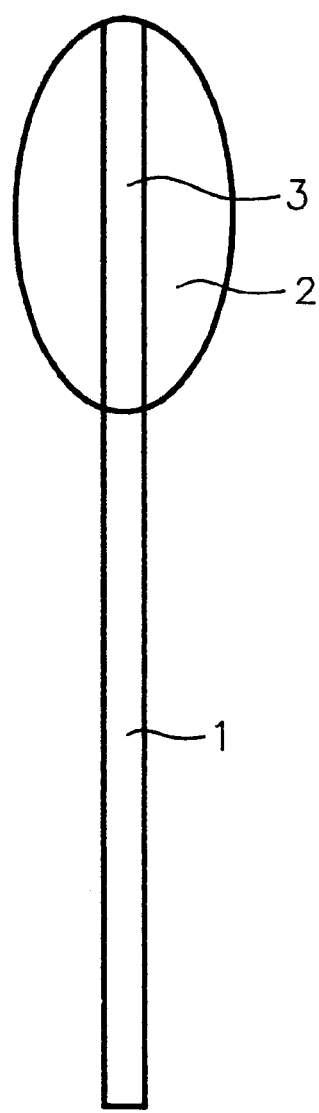

FIG. 1 illustrates a first embodiment of the invention, where the cooling device comprises a holder 1 which is used as a handle and which prevents the cooling body from being swallowed, a cooling body 2 which is soft and which contains a heat/cold-absorbing gel, and a ring 3. The holder 1 is attached to the ring 3, which is attached to the cooling body 2. The ring's function is to provide the cooling body with a certain rigidity.

FIG. 2 illustrates a second embodiment of the invention. In this embodiment the holder 1 is attached to a central plate 4 which may advantageously be heat-insulating, and which divides the cooling body into two chambers, with the result that first one and then the other chamber may be employed. It is also possible to manufacture the device with a central plate which only affects the device's rigidity.

The device can be manufactured both as a disposable device and as a multiple-use device. The device's geometry makes it easy to clean and thus no significant extra work will be required in order to use it several times.

The invention is simple and safe to use, and it solves a problem for many people suffering from problems in swallowing.

What is claimed is:

1. A cooling device for use in the treatment of problems in swallowing caused, amongst other things, by cerebral palsy or stroke, the cooling device comprising:

a body made of soft material and filled with an agent, in gel form, which can store cold, the body being designed in such a way that the body can be moved in an oral cavity and in a lip area to cool down one area at a time, the body being symmetrical in relation to a median plane, and the body being mounted on a holder in the form of a shank, the shank preventing the body from being swallowed, the body including a central plate coinciding with the median plane.

2. The cooling device according to claim 1, wherein the central plate is heat-insulating.

3. The cooling device according to claim 1, wherein the shank is attached to the central plate.

* * * * *